United States Patent
Guitard et al.

(10) Patent No.: US 9,492,416 B2
(45) Date of Patent: Nov. 15, 2016

(54) USE OF CAFTARIC ACID AND LACTIC BACTERIUM IN FOOD SUPPLEMENT FOR REGULATING SKIN PIGMENTATION

(75) Inventors: Marjorie Guitard, Savigny (CH);
Rachid Bel Rhlid, Savigny (CH);
Angus Moodycliffe, Savigny (CH);
Fabiola Dionisi, Epalinges (CH)

(73) Assignees: Nestec S.A., Vevey (CH); L'Oreal, Paris (FR)

( * ) Notice: Subject to any disclaimer, the term of this patent is extended or adjusted under 35 U.S.C. 154(b) by 83 days.

(21) Appl. No.: 13/805,887

(22) PCT Filed: Jun. 28, 2011

(86) PCT No.: PCT/EP2011/060769
§ 371 (c)(1),
(2), (4) Date: Dec. 20, 2012

(87) PCT Pub. No.: WO2012/000963
PCT Pub. Date: Jan. 5, 2012

(65) Prior Publication Data
US 2013/0095074 A1    Apr. 18, 2013

(30) Foreign Application Priority Data
Jun. 30, 2010   (EP) ..................................... 10167864

(51) Int. Cl.
| | | |
|---|---|---|
| *A01N 63/00* | (2006.01) | |
| *A61K 31/216* | (2006.01) | |
| *A61K 8/365* | (2006.01) | |
| *A61K 8/66* | (2006.01) | |
| *A61K 8/99* | (2006.01) | |
| *A61K 31/225* | (2006.01) | |
| *A61K 35/747* | (2015.01) | |
| *A61Q 19/00* | (2006.01) | |
| *A61Q 19/02* | (2006.01) | |
| *A61K 35/74* | (2015.01) | |
| *A61K 38/46* | (2006.01) | |
| *A61K 35/00* | (2006.01) | |

(52) U.S. Cl.
CPC .............. *A61K 31/216* (2013.01); *A23L 33/10* (2016.08); *A23L 33/105* (2016.08); *A23L 33/135* (2016.08); *A23L 33/17* (2016.08); *A61K 8/365* (2013.01); *A61K 8/66* (2013.01); *A61K 8/99* (2013.01); *A61K 31/225* (2013.01); *A61K 35/74* (2013.01); *A61K 35/747* (2013.01); *A61K 38/46* (2013.01); *A61K 38/465* (2013.01); *A61Q 19/00* (2013.01); *A61Q 19/02* (2013.01); *A23V 2002/00* (2013.01); *A23Y 2220/00* (2013.01); *A23Y 2240/00* (2013.01); *A23Y 2300/00* (2013.01); *A61K 2035/115* (2013.01); *A61K 2800/884* (2013.01); *A61K 2800/92* (2013.01)

(58) Field of Classification Search
None
See application file for complete search history.

(56) References Cited

U.S. PATENT DOCUMENTS

| | | | | |
|---|---|---|---|---|
| 4,671,962 | A | * | 6/1987 | Leroux .......................... 426/51 |
| 4,985,365 | A | * | 1/1991 | Mitsuda et al. .............. 435/280 |
| 5,164,185 | A | | 11/1992 | Charpin et al. |
| 6,379,716 | B2 | | 4/2002 | Santhanam et al. |
| 6,682,763 | B2 | * | 1/2004 | Kuno et al. .................... 424/769 |
| 7,112,322 | B2 | * | 9/2006 | Isolauri et al. ............ 424/93.45 |
| 8,114,658 | B2 | * | 2/2012 | Muroyama et al. ........ 435/252.9 |
| 2002/0127256 | A1 | * | 9/2002 | Murad .......................... 424/401 |
| 2007/0183996 | A1 | | 8/2007 | Okombi et al. |

FOREIGN PATENT DOCUMENTS

| | | |
|---|---|---|
| EP | 1570839 | 9/2005 |
| EP | 2210505 | 7/2010 |
| JP | 406219958 | * 8/1994 |

OTHER PUBLICATIONS

Vanzo et al. "The fate of caftaric acid administered into the rat stomach". J Agric Food Chem 2007, 55, 1604-1611.*
Publication "Phenol-Explore: Showing report on Vegetables" dated/posted Jan. 2010; p. 1-8 from webpage http://phenol-explore.eu/40 retrieved on Jun. 11, 2015.*
Guglielmetti et al. "Bacterial Cinnamoyl Esterase Activity Screening for the Production of a Novel Functional Food Product" Applied and Environmental Microbiology, Feb. 2008, vol. 74, No. 4, pp. 1284-1288.
Wang et al. "Chemical Components, Pharmacological Activity, and Advances in Development and Utilization of Plants of the Genus *Echinacea*" Journal of Chinese Medicinal Materials, Dec. 31, 2000, vol. 23, No. 12—1 page.

* cited by examiner

*Primary Examiner* — Vera Afremova
(74) *Attorney, Agent, or Firm* — K&L Gates LLP

(57) ABSTRACT

The present invention relates generally to the field of cosmetic and/or food supplement. More specifically, the present invention aims to provide the use of at least an ingredient containing caftaric acid and/or derivatives and a microorganism and/or an enzyme capable of hydrolyzing caftaric acid and/or derivatives thereof to generate tartaric and/or caffeic acid, for improving skin tone and preventing and/or treating hyper-pigmentation of skin and/or skin color imperfections such as age-spots and other skin disorders characterized by abnormal pigments. Also, the present invention aims at providing a skin lightening agent.

19 Claims, 2 Drawing Sheets

Figure 1:
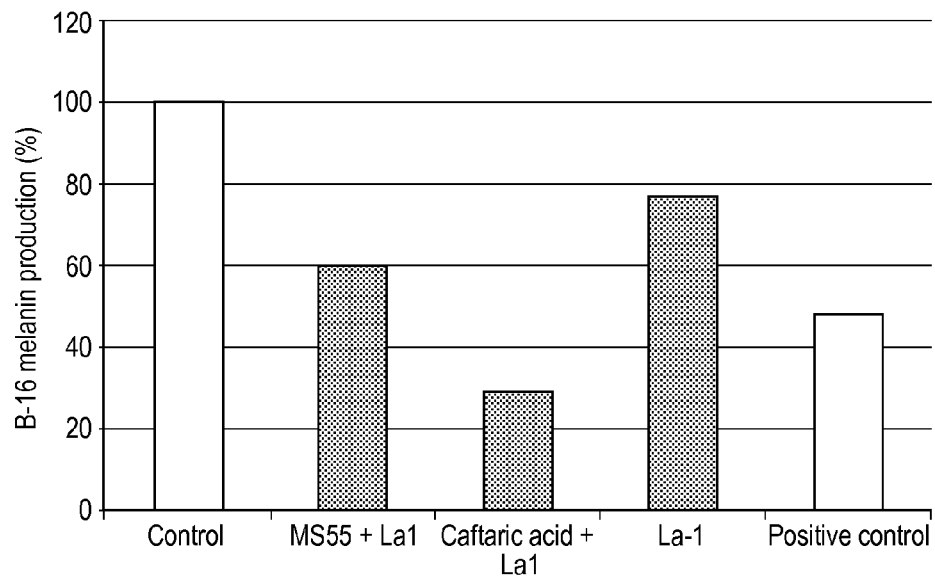

USE OF CAFTARIC ACID AND LACTIC BACTERIUM IN FOOD SUPPLEMENT FOR REGULATING SKIN PIGMENTATION

CROSS REFERENCE TO RELATED APPLICATIONS

The present application is a National Stage of International Application No. PCT/EP2011/060769, filed on Jun. 28, 2011, which claims priority to European Patent Application No. 10167864.7, filed Jun. 30, 2010, the entire contents of which are being incorporated herein by reference.

The present invention relates generally to the field of food supplements for cosmetic purpose. More specifically, the present invention aims to provide the use of an ingredient containing caftaric acid and/or derivatives and a microorganism and/or an enzyme capable of hydrolyzing caftaric acid and/or derivatives thereof to generate tartaric and/or caffeic acid, for preventing and/or treating hyper-pigmentation of skin, skin color imperfections such as age-spots and other skin disorders characterized by abnormal pigments. The present invention also aims at improving skin tone as well as providing a skin lightening or whitening agent.

BACKGROUND OF THE INVENTION

Skin color is primarily determined by the amount and type of melanin, a brown pigment present in the skin. Lower amounts of melanin result in lighter skin color while higher amounts result in darker skin color. Also, hyper-pigmentation in the skin is caused by the over expression or accumulation of melanin in the skin. As a result, the pathway involved in melanin production has been the target for many inhibitors so as to reduce the levels produced. One of the principal enzymes involved in the melanin pathway is tyrosinase.

The synthesis of melanin is a process under hormonal control, including the melanocyte stimulating hormone (MSH) and adrenocorticotropic hormone (ACTH) peptides that are produced from the precursor proopiomelanocortin. It is stimulated by the DNA damages that are caused by UVB-radiations as well.

Then, exposure to the sun over time can induce many biochemical reactions in the skin, leading to sunburn and tanning, for example. Other consequences of exposure to the sun accumulate over time. These changes can result in the development of age spots and create an uneven, mottled skin tone. Unfortunately, many of the commercially available products in today's market are either only marginally effective, or contain active agents that are unstable and lose their potency when incorporated into a final formula.

The ability to modify the expression of pigment content in the skin, to promote an evenness skin tone or lightening skin tone, is highly desired in today's society. Many people desire to modify their skin tone, to reduce aging spots, etc., or for purely cosmetic reasons.

As a result, efforts to develop effective compositions have focused on agents that inhibit the activity of tyrosinase. For example, a variety of tyrosinase inhibitors, such as hydroquinone, vitamin C, cystein, kojic acid, arbutin and glutathione among others have been proposed in topical compositions. Also, a variety of dermatological compositions have been suggested for improving the appearance of pigment disorders such as that observed in melasma, freckles, vitiligo, piebaldism, phenylketonuria, and the like, and/or for cosmetic purposes.

Also, the use of skin bleaching compositions is widely expanded. However, they either destroy melanin or inhibit its formation. Many of these contain harsh chemicals such as peroxides, acids or formaldehyde, or thiolated materials. Less stringent therapies have other disadvantages.

Topical retinoids and topical corticosteroids have been suggested as hypo-pigmenting agents, as have laser treatment and chemical peels, but these fall short of desirable responses.

Other compositions suggested the use on the skin of natural materials, which have in some cases been used for centuries in Asia or Europe to bleach skin and skin areas, or enhance the appearance of fair skin. These include the use of lemon, orange, cucumber, ginkgo, carob, rose fruit, geranium herb, cinnamon, sweet marjoram, rosemary, etc. . . . .

In order to combat disorders related to abnormal pigment or to lighten skin tone, various compounds which, when applied topically to the skin, are capable of reducing tyrosinase activity and consequently limiting melanin production, have thus been proposed. Unfortunately, the treatments currently available are not entirely satisfactory, in particular in terms of the side effects which are frequently associated therewith, such as irritant side effects with certain topical agents.

It would thus be highly desirable to have alternative preparations that do not have the drawbacks of those described in the prior art. In particular, it would be highly desirable to develop nutritional cosmetic compositions to be administered via oral route that have improved stability and efficacy to promote an evenness skin tone or to lighten skin tone.

There also remains a need to active agents that are effective for treating and/or preventing skin pigmentation disorders, in particular those due to environmental factors or aging.

The object of the present invention is to meet these needs.

SUMMARY OF THE INVENTION

The present inventors could achieve this object by providing a food supplement composition that comprises at least one ingredient containing caftaric acid and/or derivatives and a lactic bacterium and/or an enzyme capable of hydrolyzing caftaric acid and/or derivatives thereof to generate tartaric and/or caffeic acid.

Thus, according to a first subject, the invention relates to the cosmetic use of least one ingredient containing caftaric acid and/or derivatives and a lactic bacterium and/or an enzyme capable of hydrolyzing caftaric acid and/or derivatives thereof to generate tartaric and/or caffeic acid, for treating and/or preventing skin pigmentation disorders. Such skin disorder are in particular those due to age or to environmental factors (e.g. UV), such as age-spots. It may also be skin disorders that are observed in melasma, freckles, vitiligo, piebaldism, phenylketonuria, and the like.

The present inventors have discovered that ingredient containing caftaric acid treated with a lactic bacterium effectively suppress the formation of melanin, melanogenesis, despite the fact that the extracts show little to no inhibition of tyrosinase activity. This result is surprising and unexpected considering the pivotal role of tyrosinase in melanogenesis and the focus of development efforts in the art to inhibit this enzyme.

For the purpose of the present invention, the term "skin" is intended to mean the skin of the face or of the body.

For the purpose of the present invention the term "effective amount", is intended to mean an amount sufficient to obtain the expected effect.

For the purpose of the present invention the term "prevent" is intended to mean the fact of reducing the risk of occurrence of the manifestation of the disorder under consideration.

The present invention is also directed towards the cosmetic use of the abovementioned ingredient, as an active agent for treating and/or composition for preventing the skin imperfections, in particular to improve skin tone or skin complexion.

The present invention is also directed towards the cosmetic use of the abovementioned ingredient, as an active agent for treating and/or preventing the skin pigment imperfections. As a result, the complexion becomes brighter and more homogeneous, without areas of dyschromia or of dryness.

The present invention is also directed towards the cosmetic use of an effective amount of at least one ingredient containing caftaric acid and/or derivatives and a lactic bacterium and/or an enzyme capable of hydrolyzing caftaric acid and/or derivatives thereof to generate tartaric and/or caffeic acid, as an active agent for whitening or lightening skin tone.

The present inventors have also discovered that the ingredient according to the invention further improves hydration and/or skin barrier function.

A use in accordance with the present invention may also comprises the use of at least one ingredient containing caftaric acid and/or derivatives and a lactic bacterium and/or an enzyme capable of hydrolyzing caftaric acid and/or derivatives thereof to generate tartaric and/or caffeic acid, in combination with an effective amount of at least one active agent for further improving skin hydration or skin ageing, in particular as described hereinafter.

According to another of its aspects, the subject of the invention is a method, in particular a cosmetic method, for treating and/or preventing skin tone imperfections and the disorders associated with hyper-pigmentation, in particular aesthetic disorders, in an individual, comprising at least one step of administering, to said individual, at least one ingredient containing caftaric acid and/or derivatives and a lactic bacterium and/or an enzyme capable of hydrolyzing caftaric acid and/or derivatives thereof to generate tartaric and/or caffeic acid.

Compositions according to the present invention are orally administrable. This has the advantage of acting globally on the entire skin, in its deep layers (dermis, hypodermis), by means of a rapid and relatively non-restrictive mode of administration. Specifically, the metabolites and other active nutriments are in particular distributed within the dermal matrix by means of the bloodstream. Oral administration also has the advantage of a rapid and relatively non-restrictive mode of administration.

DETAILED DESCRIPTION OF THE INVENTION

Ingredient Containing Caftaric Acid and or Derivatives

Caftaric acid is

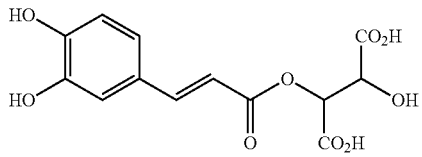 [SMILES: O=C(/C=C/c1ccc(O)c(O)c1)OC(C(=O)O)C(O)C(=O)O]

and its derivatives include compounds which exhibit at least one $C_1$-$C_3$ alkylation of an OH-group and/or a $CO_2H$-group. For example both phenolic OH-groups may be alkylated. Alternatively and/or additionally both carboxyl groups may be transformed into the corresponding alkylesters. In one embodiment all OH-groups and all $CO_2H$-groups are alkylated.

Typical derivatives are compounds in which both phenolic OH-groups are methylated, and/or compounds in which both carboxyl groups are methylated.

Further typical derivatives include compounds with the following formula

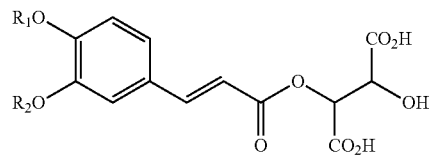

wherein $R_1$ and/or $R_2$ are selected from the group consisting of H; $CH_3$; aryl, such as phenyl, benzyl, tolyl, o-xylylalkyl; $C_1$-$C_3$-acyl, amino acids, monosaccharides. $R_1$ and/or $R_2$ may be identical or may differ from each other.

One caftaric acid derivative is the following compound:

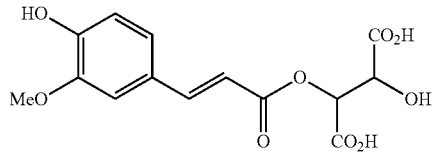 [SMILES: COc1cc(/C=C/C(=O)OC(C(=O)O)C(O)C(=O)O)ccc1O]

The ingredient containing caftaric acid and/or derivatives thereof may be any ingredient that contains caftaric acid and/or derivatives thereof, either naturally or in added form, but is preferably a natural foodstuff such as lettuce, chicory, dandelion, grape, grape pomace; or combinations or extracts thereof.

In an embodiment, the plant material is added to the oral cosmetic composition in the form of an extract, such as a chicory extract. The chicory extract can be made from any suitable part of the plant material includes, for example, the root, the pulp, the like or combinations thereof.

Suitable extracts of chicory for the purpose of the present invention are also extracts that are commercially available, such as for example Leroux MS55 (commercially available from Leroux SAS, France).

In a particular preferred embodiment of the present invention, suitable extracts of chicory may be prepared by any means that are known in the art, e.g., by steam extraction, solvent extraction, distillation, pressing or grinding. In particular, the extract is obtainable by extraction with a solvent from Chicory plant material, by a water extraction or an alcohol/water extraction, for example by a ethanol/water extraction or methanol/water extraction. The extract can be used as liquid (e.g. Leroux MS55, Leroux MS70) or as powder form (e.g. Leroux Sol B).

For ease of handling, the plant material is preferably in a dried and comminuted or powder form. As described below, the processes utilize dried, comminuted chicory and/or extracts thereof. However, it is to be understood that any suitable plant material may be used in any suitable form and added to the product according to the present invention.

The extract is processed such that its flavor can be enhanced. For example, bitter flavors which are typically associated with plant materials, such as chicory, can be removed by processing the plant into an extract. The extract can also be prepared such that the amount of bioactive agent in the final extract product can be desirably controlled.

It should be appreciated that the plant material can be processed to form an extract in a variety of different and suitable ways. In general, the plant material, such as the chicory root, is ground, powdered or provided in any suitable form. The plant material can then be further processed in a number of different stages to produce the product extract. In an embodiment, a defatting procedure is performed on the plant material to produce an extract that results from fats removed from the plant material. The defatting procedure can be conducted under any suitable defatting process conditions with any suitable types and amounts of solvents including, for example, hexane.

In an embodiment, the resultant extract of the defatting procedure can be further processed via acid hydrolyzis to produce another type of plant extract that can be added to the nutritional composition of the present invention. The acid hydrolyzis procedure can be conducted under any suitable process condition with any suitable types and amounts of solvents, including, for example, ethyl acetate.

In an embodiment, the extract from the defatting procedure can be further processed via a solvent extraction procedure. The solvent extraction can be carried out under any suitable process conditions and in the presence of any suitable amount and type of solvent. In an embodiment, the solvent includes a solution of methanol ("MeOH") and water mixed in a 1:1 volume ratio. The resultant solution of the solvent extraction procedure can be further processed by evaporation of the solvent under suitable conditions to produce another extract. Alternatively, the resultant solution can be treated with an adsorbant agent, such as polyvinylpolypyrrolidone or the like, to trap polyphenols. The adsorbant agent treatment can be carried out under any suitable process conditions.

The amount of Caftaric acid or a plant extract containing it, in the product will depend on several factors, such as the nature of the extract, the condition of the plant, the age, condition and size of the person or animal to be treated, the frequency, the product will be administered and/or the specific kind of skin disorder or damage to be treated or prevented or desired cosmetic effect.

The present inventors have found that the effectiveness of caftaric acid or an extract containing it according to the present invention is generally dose dependant and follows a dose response curve. If generally mild skin disorders or damages are to be prevented and the product will be used frequently, very small amounts of caftaric acid or an extract thereof will be sufficient to achieve the desired effect. If a severe skin pigment disorder is to be treated, larger amounts of the ingredient will be more appropriate, although also small amounts will produce an effect.

In a preferred embodiment the ingredient is enriched in caftaric acid and/or derivatives thereof. For example, the ingredient and/or the composition may comprise caftaric acid and/or derivatives thereof in an amount in the range of 0.001-99.99 weight-% of dry weight, preferably 0.1-50 weight-% of dry weight, most preferred 0.1-10 weight-% of dry weight. The ingredient and/or the composition may comprise the micro-organism and/or the enzyme capable of hydrolysing caftaric acid and/or derivatives thereof to generate tartaric and/or caffeic acid in an amount in the range of 0.001-99.99 weight-% of dry weight, preferably 0.1-50 weight-% of dry 10 weight, most preferred 0.1-10 weight-% of dry weight.

Generally, it is preferred if the product contains chicory or an extract thereof in an amount in the range of about 0.1 g/l to 10 g/l, preferably in the range of 0.5 g/l to 3 g/l product. If the total amount of product cannot be measured in liters it is preferred if the product contains chicory or an extract thereof in an amount in the range of about 0.1 g/kg to 10 g/kg, preferably in the range of 0.5 g/kg to 3 g/kg product.

Preferably the product contains chicory or an extract thereof in a daily dose of 0.01 g-100 g, preferably 0.25 g-10 g.

The ingredient to be mixed with the ingredient containing caftaric acid and/or derivatives thereof comprises a lactic acid bacterium and/or an enzyme capable of hydrolyzing caftaric acid and/or derivatives thereof to generate tartaric and/or caffeic acid. These two ingredients may be mixed briefly prior to consumption or may be provided as a ready-to-consume composition.

Microorganisms or Enzyme Capable of Hydrolyzing Caftaric Acid

Caftaric acid and/or its derivatives can then be hydrolyzed by a lactic acid bacterium capable of hydrolyzing caftaric acid and/or derivatives thereof. This hydrolyzis step will generate tartaric and/or caffeic acid.

Without wishing to be bound by theory, the inventors believe that this hydrolyzis occurs as outlined in the following scheme. Note, that all reaction steps catalyzed by "enzyme" may also be catalyzed by the lactic acid bacterium described in the present application and/or by combinations of lactic acid bacterium and enzymes.

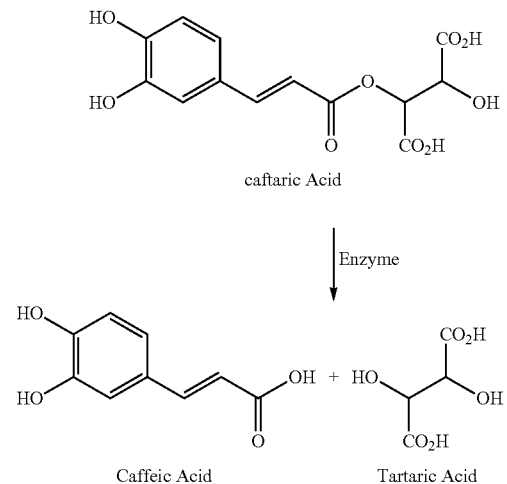

caftaric Acid

Enzyme

Caffeic Acid        Tartaric Acid

The inventors have surprisingly found that treating an ingredient comprising caftaric acid and/or derivatives thereof with lactic acid bacterium or an enzyme capable of hydrolyzing caftaric acid and/or derivatives thereof to generate tartaric and/or caffeic acid results for example in improved activity of the ingredient.

Furthermore, it has been found that this treatment can take place in vivo when a human or an animal ingests a composition comprising caftaric acid and/or derivatives thereof in combination with a lactic acid bacterium capable of hydrolyzing chlorogenic acids to generate phenolic acids.

Preferred lactic acid bacterium capable of hydrolyzing caftaric acid and/or derivatives thereof to generate tartaric and/or caffeic acid are probiotic lactic acid bacterium having a esterase activity, such as chlorogenate esterase and/or feruloyl esterase, preferably *Lactobacillus* or *Bifidobacterium*, for example *L. johnsonii, B. longum,* and *B. lactis* (CNCM I-3446), even more preferred *Lactobacillus johnsonii* La1 (CNCM I-1225), *B. longum* BB 536, and *B. lactis* BB12.

*B. longum* BB 536 is commercially available from Morinaga Nutritional Foods, Inc.

*B. lactis* BB12 is commercially available, e.g., from Chr. Hansen, DK-2970 Horsholm.

In one embodiment of the present invention, the lactic acid bacterium may be used in a non-replicating form.

The ability of a lactic acid bacterium or of a fraction thereof to hydrolyze caftaric acid may be tested as described in detail for *L. johnsonii* CNCM I-1225 (see examples).

In another embodiment, an enzyme capable of hydrolyzing caftaric acid to generate tartaric and/or caffeic acid is further added to the lactic acid bacterium. Preferably, such enzyme is selected from the group consisting of esterases, such as chlorogenate esterase, tannase and/or feruloyl esterase. It may be added in an amount such as preferably at least 5%, such as at least 30%, at least 50%, or at least 75% of caftaric acid present in the composition is hydrolyzed prior to and/or during consumption.

Suitable enzymes that can be used in the framework of the present invention include e.g. esterases, e.g. chlorogenate esterase derived from *Aspergillus japonicus*. (Commercially available from Kikkoman, Japan), tannase from *Aspergillus oryzae* (EC 3.1.1.20) (commercially available from Kikkoman, Japan). The enzyme may be present as a purified enzyme (immobilized or not) or e.g. in the form of a cell lysate of a microorganism. Suitable cells may e.g. be cells of the microorganisms mentioned above. Suitable methods for producing cell lysate are known in the art.

The composition and/or ingredients of the invention should be formulated such that the lactic acid bacterium strain will not ferment or react with the composition during storage. This may be achieved e.g. by formulating the composition as a dry powder, and/or by encapsulating the lactic acid bacterium so that it will only be released when the composition is mixed with at least one other ingredient or during digestion.

The lactic acid bacterium should be present in an amount sufficient for hydrolyzing a substantial amount of caftaric acid to generate tartaric and/or caffeic acid during digestion. The amount of lactic acid bacterium and/or enzyme needed may e.g. be determined by those skilled in the art, for example dependent on the subject to be treated or on the speed by which the tartaric and/or caffeic acid should be liberated. Preferably at least 5%, such as at least 30%, at least 50%, or at least 75% of caftaric acid present in the composition is hydrolyzed prior to and/or during consumption.

The compositions according to the invention may be in any of the galenical forms usually available for the method of administration selected.

Galenical Forms

The compositions according to the invention may be in any of the galenical forms normally available for the method of administration selected. The carrier may be of diverse nature depending on the type of composition under consideration.

Food supplement for oral administration may be present in capsules, gelatin capsules, soft capsules, tablets, sugar-coated tablets, pills, pastes or pastilles, gums, or drinkable solutions or emulsions, a syrup or a gel. Such a supplement might also include a sweetener, a stabilizer, an antioxidant, an additive, a flavouring agent and/or a colorant. The formulation thereof is carried out by means of the usual methods for producing sugar-coated tablets, gel capsules, gels, hydrogels for controlled release, emulsions, tablets or capsules.

In one embodiment the invention relates to a kit for treating and/or preventing skin pigment disorders and/or skin imperfections, comprising an oral treatment with a composition containing at least an ingredient containing chicoric acid and/or derivatives and a lactic acid bacterium and/or an enzyme capable of hydrolyzing chicoric acid to generate tartaric and/or caffeic acid in a food supplement, combined with an oral food supplement or topical composition optionally containing a probiotic microorganism in dead, live or semi-active form, or an hydrating or anti-ageing agent.

The kit for preparing a food supplement comprises at least two parts:
 a) a first part comprising a chicoric acid and/or derivatives thereof containing ingredient; and
 b) a second part comprising a lactic acid bacterium and/or an enzyme capable of hydrolyzing chicoric acid and/or derivatives thereof to generate tartaric and/or caffeic acid.

Those skilled in the art will understand that they can freely combine all features of the present invention described herein, without departing from the scope of the invention as disclosed. In particular, features described for the uses of the present invention may be applied to the composition and/or the kit of the present invention and vice versa.

Use

The products of the invention may be efficiently used for treating or preventing skin pigmentation disorders or cosmetically lightening skin tone e.g. by decreasing the production of melanin. Indeed ingredient containing caftaric acid treated with probiotic bacterium La-1 was shown to decrease in vitro the synthesis of melanin (Example 1, FIG. 1). The production of tyrosinase was also decreased but to a limited extent (FIG. 2), suggesting that the decrease in melanin was not due to tyrosinase inhibition but rather to mechanisms acting upstream or downstream of this enzyme.

The compositions according to the present invention have further a positive effect on strengthening skin barrier and maintaining skin hydration.

As a result, the pigment imperfections are reduced, the complexion becomes brighter and more homogeneous, without areas of dyschromia, or of dryness.

Thus, according to one subject, the invention relates to the cosmetic use of an effective amount of at least one ingredient containing caftaric acid and/or derivatives and a lactic bacterium and/or an enzyme capable of hydrolyzing caftaric acid and/or derivatives thereof to generate tartaric and/or caffeic acid, as an active agent for treating and/or preventing skin pigmentation disorders, in particular those due to age or environmental factors such as UV.

The present compositions may also be used as active agent for whitening or lightening skin tone, which is particularly desirable for asian population.

A use in accordance with the present invention may also comprises the use of the compositions, in combination with an effective amount of at least one active agent for improving skin hydration or skin ageing, in particular as described hereinafter.

According to another of its aspects, the subject of the invention is a method, in particular a cosmetic method, for treating and/or preventing skin tone imperfections and the disorders associated with hyper-pigmentation, in particular aesthetic disorders, in an individual, comprising at least one step of administering, to said individual, compositions as described above.

The cosmetic treatment method of the invention may be carried out in particular by orally administering the composition as described above. Oral administration comprises ingesting, in one or more intakes, an oral composition as defined above.

It may comprise a single application. According to another embodiment, the application is repeated, for example, 2 to 3 times a day, for one day or more, and generally for a sustained period of at least 4, or even 1 to 15, weeks.

In addition, combinations of treatment with, optionally, oral or topical forms may be envisaged in order to supplement or reinforce the activity of the compositions as defined by the invention.

Thus, a topical or oral treatment with a composition containing caftaric acid in accordance with the invention, combined with an oral or topical composition optionally containing another active ingredient, in particular a probiotic microorganism, or other probiotics in dead, live or semi-active form or a hydrating or anti-ageing agent could be imagined as a kit. The ingredients are mixed, before they are formulated, in the order and under conditions readily determined by those skilled in the art.

The ingredients are mixed, before they are formulated, in the order and under conditions readily determined by those skilled in the art.

Further advantages and features of the present invention are apparent from the following Examples and Figures. The examples hereinafter are thus presented by way of non-limiting illustration of the field of the invention. In these examples, unless otherwise indicated, the percentages are percentages by weight and the ranges of values written in the form "between . . . and . . . " include the upper and lower limits specified. The term "cfu" denotes "colony forming unit". This is the unit of measurement used to quantify live bacteria.

FIGURES

FIG. 1: Melanin production by murine melanocytes pre-treated with caftaric acid+La1 vs. controls (positive/negative).

Figure 2:
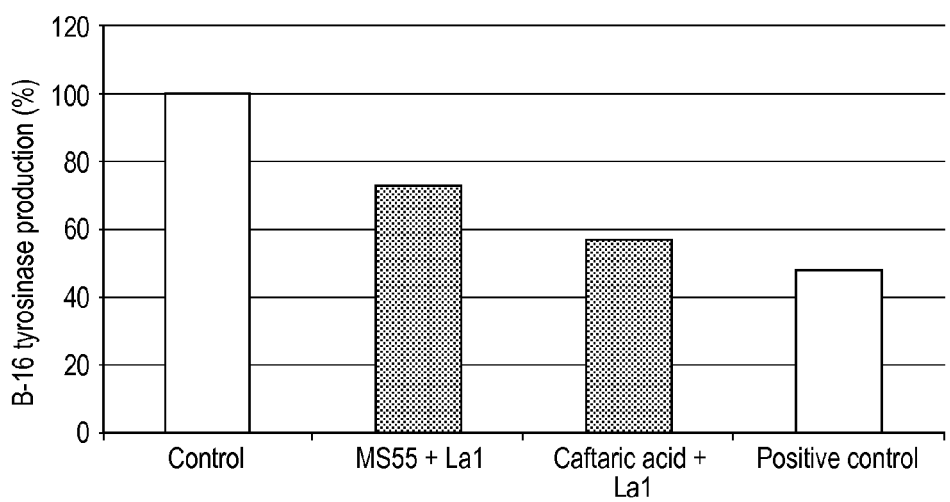

FIG. 2: tyrosinase production by murine melanocytes pre-treated with caftaric acid+La1 vs. controls (positive/negative).

Figure 3:
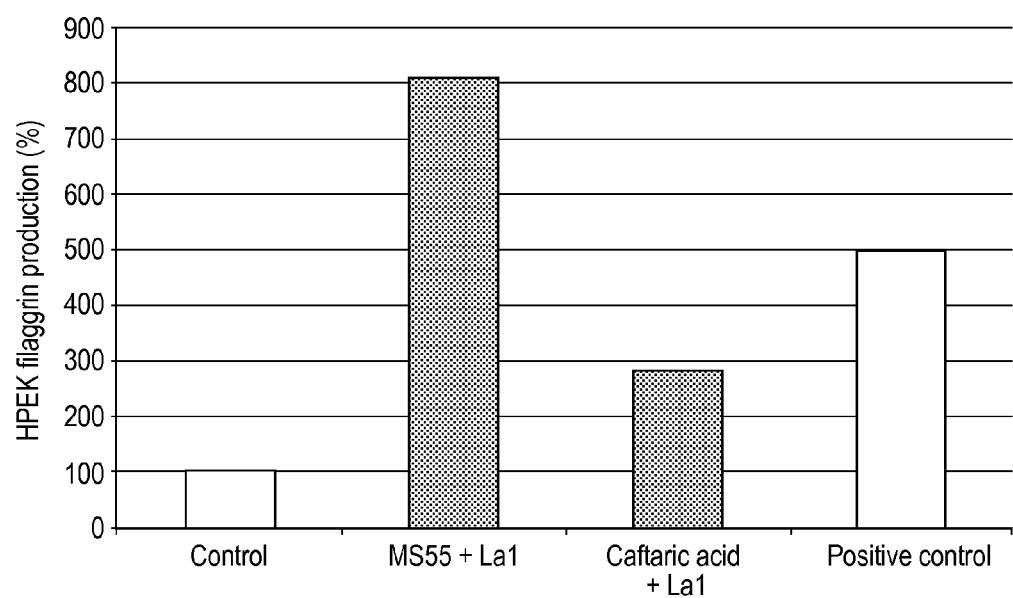

FIG. 3: Filaggrin synthesis by human primary epidermal keratinocytes pre-treated with caftaric acid+La1 vs. controls (positive/negative).

EXAMPLES

Example 1

Hydrolyzis of Caftaric Acid

1—Hydrolyzis of Caftaric Acid with Chlorogenate Esterase

A solution of chlorogenate esterase (0.8 mg, 24 U/g, from Kikkoman Japan) in 100 µl phosphate buffer (50 mM, pH 7.0) was added to a solution of caftaric acid (0.57 mg) in 100 µl phosphate buffer (50 mM, pH 7.0). The mixture was then incubated at 37° C. for 4 h. After the reaction time, the enzymatic activity was stopped by heat treatment (5 min, 90° C.) and the mixture was centrifuged (microcon YM10, 30 min, 14000 g). The supernatant was then analysed by HPLC. A control reaction was run in parallel under the same reaction conditions but without enzyme.

2—Hydrolyzis of Caftaric Acid with *L. johnsonii* (La1)

Cells of *L. johnsonii* (CNCM I-1225) were grown (7.0 E08 cfu/ml) and centrifuged (5000 g, 10 min), the pellets were resuspended in phosphate buffer (50 mM, pH 7.0) at a concentration of 0.61 g/ml. To 100 µl of this cells solution, 100 µl of a solution of caftaric acid (12 mM) was added and the mixture was incubated at 37° C. Samples were withdrawn at different reaction times, centrifuged (3000 g, 5 min), filtered through 0.45 µm pore size syringe filters (Millipore SLHA 025 BS) and analysed by HPLC.

A control reaction was run in parallel under the same reaction conditions but without bacterium.

3—Hydrolyzis of Caftaric Acid with *L. johnsonii* Extract (Lysed Cells)

Cells of *L. johnsonii* (CNCM I-1225) were grown (7.0 E08 cfu/ml) and centrifuged (5000 g, 10 min), the pellets were resuspended in phosphate buffer (50 mM, pH 7.0) at a concentration of 0.61 g/ml. The cells were then lysed using the glass-beads method. 600 µl of cells preparation were put into a Mini-Beadbeater for 1 min of intense shaking, cooled in ice, and put another 1 min in the Mini-Beadbeater. The crude cell extract (100 µl) was then added to 100 µl of a solution of caftaric acid (12 mM, phosphate buffer 50 mM, pH 7.0) and the mixture was incubated at 37° C. Samples were withdrawn at different reaction times, centrifuged (3000 g, 5 min), filtered through 0.45 µm pore size syringe filters (Millipore SLHA 025 BS) and analysed by HPLC.

4—Hydrolyzis of Caftaric Acid with a Spray-Dried Preparation of La1

10 mg of a spray-dried preparation of La1 (3.3 E09 cfu/g) were dissolved in 100 µl of phosphate buffer (50 mM, pH 7.0). To this solution, 100 µl of a caftaric acid solution (12 mM, phosphate buffer 50 mM, pH 7.0) were added. The mixture was then incubated at 37° C. and samples were withdrawn at different reaction times. After centrifugation (3000 g, 5 min) and filtration (0.45 µm pore size syringe filters, Millipore SLHA 025 BS) the samples were analysed by HPLC.

HPLC Analysis

HPLC-DAD analysis of caftaric acid and hydrolyzis products was performed on Agilent 1100 system equipped with Atlantis C18 reverse-phase column (4.6×100 mm, particle size 3 µm) and a diode array detector. The column was equilibrated with water containing 0.1% formic acid. After injection, a linear gradient to a final solvent composition of 55% water and 45% acetonitrile (containing 0.1% formic acid) was run within 12 min at a flow rate of 1 ml/min. Caftaric acid and caffeic acid were monitored by UV at 320 nm and were quantified using standard calibration curves.

Results

Tested Bacteria

TABLE 1

| Bacteria | Culture Media |
| --- | --- |
| *Lactobacillus rhamnosus* GG (NCC 4007) | MRS |
| *Lactobacillus johnsonii* La1 (CNCM I-1225) | MRS |
| *Lactobacillus paracasei* ST11 (NCC 2461) | MRS + Cysteine |
| *Bifidobacterium longum* BB 536 (ATCC BAA-999) | MRS + Cysteine |
| *Bifidobacterium lactis* BB12 (CNCM I-3446) | MRS |
| *Streptococcus thermophilus* TH4 (NCC 2496) | HJL |

In particular *L. johnsonii* (La1), *B. longum* BB 536, and *B. lactis* BB12 were able to hydrolyze caftaric acid. The best results in term of reaction rate and reaction yield were obtained with *L. johnsonii* (La1)

Tested Enzymes

TABLE 2

| Enzyme | Supplier |
| --- | --- |
| Chlorogenate esterase | Kikkoman, Japan |
| Feruloyl esterase | Novozymes |
| Porcine liver esterase | Sigma E-3019 |
| Hog liver esterase immobilised on Eupergit C | Fluka 46064 |
| Esterase from *Saccharomyces cerevisiae* | Fluka 46071 |
| Esterase from *L. johnsonii* | Internal production |

Only chlorogenate and feruloyl esterases were able to hydrolyze caftaric acid into caffeic and tartaric acids 1—Hydrolyzis of Caftaric Acid with Chlorogenate Esterase

TABLE 3

Hydrolyzis of caftaric acid into caffeic and caftaric acids by chlorogenate esterase. Concentration in % relative to untreated reference at t = 0

| Time (min) | 0 | 15 | 30 | 60 | 120 | 240 |
| --- | --- | --- | --- | --- | --- | --- |
| caftaric Acid | 99 | 82 | 64 | 43 | 19 | 2 |
| Caffeic Acid | 0 | 18 | 36 | 57 | 81 | 98 |

2—Hydrolyzis of Caftaric Acid with La1 Fresh Cells

After 4 h reaction time all caftaric acid was transformed into caffeic acid and tartaric acid as analysed by HPLC 3—Hydrolyzis of Caftaric Acid with La1 Extract (Lysed Cells)

As compared to whole cells, the hydrolyzis of caftaric acid with lysed cells resulted in an increase of the reaction rate. Indeed, after only 2 h all caftaric acid was transformed into caffeic acid and tartaric acid.

4—Hydrolyzis of Caftaric Acid with a Spray-Dried Preparation of La1

TABLE 4

Hydrolyzis of caftaric acid into caffeic and caftaric acids by a spray-dried preparation of *L. johnsonii*. Concentration in % relative to untreated reference at t = 0

|  | 0 min | 15 min | 30 min | 1 h | 2 h | 3 h |
| --- | --- | --- | --- | --- | --- | --- |
| Caftaric Acid | 99 | 68 | 47 | 24 | 8 | 2 |
| Caffeic Acid | 0 | 32 | 53 | 76 | 92 | 98 |

Example 2

Effect on Skin Pigmentation

In order to evaluate the potential beneficial effect of ingredients towards skin de- or pro-pigmentation we used 2D culture of murine melanocytes (B16) and we performed 2 tests: 1—assessment of melanin production and 2—assessment of tyrosinase production.

1. The Cell Culture Conditions.
   B16 cells were cultured in DMEM 1 g/L glucose without phenol red supplemented with 10% foetal calf serum, in a humidified chamber at 37° C. and containing 5% $CO_2$.

2. The Production of Melanin by B16 Murine Melanocyte Cell Line.
   Cells were incubated with the selected ingredients or the test references (Kojic acid at 400 µg/mL) for 72 hours, in the presence or absence of NDP-MSH an analog of MSH. The total quantity of melanin (extracellular and intracellular) was evaluated by measurement of the optical density at 405 nm of each sample against melanin standards in presence or in absence of NDP-MSH.

3. The Production of Tyrosinase by B16 Murine Melanocyte Cell Line.
   Cells were incubated with the selected ingredients or the test references (Kojic acid at 400 µg/mL) for 48 hours. The production of tyrosinase was evaluated by immunolabeling.

Ingredients:
The selected ingredients are listed in the Table 5 below. Caftaric acid has been pre-treated with La-1 [(spray dried culture *Lactobacillus Johnsonii* CNCM I-1225, 1.19E10 cfu/g) for 24 hours in a thermomixer at 40° C., under shaking conditions. After incubation, samples have been centrifuged 5 minutes at 3000 g. After this treatment the probiotic as such is not present anymore in the sample however the presence of its metabolites can't be excluded. The tested concentrations of caftaric acid are also indicated in Table 5.

TABLE 5

| Ingredient | Highest non cytotoxic conc. on HDF (mg/mL) | Highest non cytotoxic conc. on HPEK (mg/mL) | Tested conc. on HDF (mg/mL) | Tested conc. on HPEK (mg/mL) |
| --- | --- | --- | --- | --- |
| MS55 10 mg/ml in NaPO4 10 mM pH 7.0 + 10 mg/ml La1 | 2 | 10 | 0.4 | 10 |
| Caftaric acid 10 mM ie 3.12 mg/ml + 90 mg La1 | 0.2 mM | 0.04 mM | 0.2 mM | 0.04 mM |
| La-1 (10EE11 cfu/g) | 0.01 | 0.01 | 0.01 | 0.01 |

Results

Results are expressed in percentage relative to the control. Test reference (Kojic acid) induced, as expected, a decrease in melanin production. FIG. 1 shows the melanin production by B16 melanocytes treated for 72 hours with the selected ingredients. Caftaric acid treated with the probiotic CNCM I-1225 appeared to be efficient for skin de-pigmentation. Indeed caftaric acid treated with the probiotic decreased melanin production by 70% (FIG. 1). The production of tyrosinase was also decreased by this ingredient but to a limited extent (approximately 40%, FIG. 2), suggesting that the decrease in melanin was only partially due to tyrosinase inhibition. Additional mechanisms acting upstream or downstream of this enzyme may exist.

Example 3

Effect on Skin Barrier Function and Hydration

The potential beneficial effect of the Extracts of Example 2 towards skin barrier function and skin hydration was evaluated by using 2D culture of human primary epidermal keratinocytes and we assessed their synthesis of filaggrin after treatment with the selected ingredients.

The Cell Culture Conditions.

Human epidermal keratinocytes were cultured in control keratinocytes-SFM medium, in a humidified chamber at 37° C. and containing 5% CO2.

The Synthesis of Filaggrin by Human Epidermal Keratinocytes.

Cells were incubated with the selected ingredients or the test references (CaCl2 at 1.5 mM) for 144 hours. The production of filaggrin by was evaluated by immunolabeling.

Results

The results are shown in FIG. 3. Pre-treatment of the cells with caftaric acid+La1 showed a significant increase of filaggrin (280% of the control, FIG. 3), suggesting that these extracts could strengthen skin barrier. A stronger skin barrier ensures a better protection of the body from the environment and pathogens' attack. It also limits the loss of water through the epidermis, thus ensuring an appropriate skin hydration.

Example 4

Capsule

| Ingredients | Amount mg/capsule |
| --- | --- |
| Chicory extract | 300 |
| *Lactobacillus jonhsonii* CNCM I-1225 | $10^9$ cfu |
| Vitamin C | 60 |
| Magnesium stearate | 0.02 |

One to three of these capsules can be taken per day.

The invention claimed is:

1. A method for treating skin pigment disorders and/or skin pigment imperfections in an individual in need thereof, said disorders and imperfections being associated with hyperpigmentation, comprising administering orally a food supplement comprising at least (i) a daily dose of 0.01 g-100 g of an ingredient containing an amount of 0.1-50 weight % of dry weight of caftaric acid and/or derivatives thereof, and (ii) an amount of 0.1-50 weight % of dry weight, as compared to the dry weight of the food supplement, of a lactic acid bacterium and/or an enzyme capable of hydrolyzing caftaric acid to generate, during digestion, tartaric and/or caffeic acid, said individual in need thereof having a disorder and/or imperfection associated with hyperpigmentation, and said lactic acid bacterium and/or enzyme capable of hydrolyzing caftaric acid being administered in an adapted amount for sufficient hydrolysis of the caftaric acid.

2. Method in accordance with claim 1, wherein the skin disorders are selected from the group consisting of melasma, freckles, and age spots.

3. Method in accordance with claim 1 for improving skin tone and/or skin complexion.

4. A method for lightening and/or whitening skin tone in an individual in need thereof comprising administering orally a food supplement comprising at least (i) a daily dose of 0.01 g-100 g of an ingredient containing an amount of 0.1-50 weight % of dry weight of caftaric acid and/or derivatives thereof, and (ii) an amount of 0.1-50 weight % of dry weight, as compared to the dry weight of the food supplement, of a lactic acid bacterium and/or an enzyme capable of hydrolyzing caftaric acid to generate, during digestion, tartaric and/or caffeic acid, said an individual being in need of lightened and/or whitened skin tone, and said lactic acid bacterium and/or enzyme capable of hydrolyzing caftaric acid being administered in an adapted amount for sufficient hydrolysis of the caftaric acid.

5. Method in accordance with claim 1, wherein the composition improves hydration of the skin and/or skin barrier function.

6. Method in accordance with claim 1, wherein the caftaric acid containing ingredient is a natural foodstuff.

7. Method in accordance with claim 1, wherein the food supplement comprises an enzyme capable of hydrolyzing caftaric acid to generate, during digestion, tartaric and/or caffeic acid.

8. Method in accordance with claim 1, wherein the lactic acid bacterium capable of hydrolyzing caftaric acid to generate, during digestion, tartaric and/or caffeic acid is a probiotic lactic acid bacterium having an esterase activity.

9. Method in accordance with claim 1, wherein the lactic acid bacterium is selected from the group consisting of *L. johnsonii, B. longum*, and *B. lactis*.

10. Method in accordance with claim 1, wherein the food supplement further comprises an effective amount of at least one active agent for improving skin hydration or skin ageing.

11. Method in accordance with claim 4, wherein the caftaric acid containing ingredient is a natural foodstuff.

12. Method in accordance with claim 4, wherein the food supplement comprises an enzyme capable of hydrolyzing caftaric acid to generate, during digestion, tartaric and/or caffeic acid.

13. Method in accordance with claim 4, wherein the lactic acid bacterium is selected from the group consisting of *L. johnsonii, B. longum*, and *B. lactis*.

14. Method in accordance with claim 1, wherein the lactic acid bacterium is selected from the group consisting of *Lactobacillus johnsonii* (CNCM I-1225), *B. longum* BB 536, *B. lactis* (CNCM I-3446) and *B. lactis* BB12.

15. Method in accordance with claim 4, wherein the lactic acid bacterium is selected from the group consisting of *Lactobacillus johnsonii* (CNCM I-1225), *B. longum* BB 536, *B. lactis* (CNCM I-3446) and *B. lactis* BB12.

16. Method in accordance with claim 1, wherein the oral administration of said food supplement is repeated 2 to 3 times a day, for at least 4 weeks.

17. Method in accordance with claim 1, wherein the ingredient containing caftaric acid is Chicory or an extract thereof.

18. Method in accordance with claim 1, wherein the ingredient containing caftaric acid is an extract of Chicory root.

19. Method in accordance with claim 1, wherein the oral administration of said food supplement is repeated 2 to 3 times a day, for at least 4 weeks.

* * * * *